United States Patent [19]

DiCosimo et al.

[11] Patent Number: 4,721,789

[45] Date of Patent: Jan. 26, 1988

[54] OXIDATIVE CYCLIZATION OF 2-METHYLGLUTARONITRILE TO 3-CYANOPYRIDINE

[75] Inventors: Robert DiCosimo, Shaker Heights; James D. Burrington, Richmond Heights; Robert K. Grasselli, Chagrin Falls, all of Ohio

[73] Assignee: The Standard Oil Company, Cleveland, Ohio

[21] Appl. No.: 678,433

[22] Filed: Dec. 5, 1984

[51] Int. Cl.⁴ .......................................... C07D 213/85
[52] U.S. Cl. .................................... 546/250; 546/286
[58] Field of Search ............................. 546/286, 250

[56] References Cited

U.S. PATENT DOCUMENTS 4,057,552  11/1977  Richtzenhain ................... 546/250

OTHER PUBLICATIONS

Emmett, P. H., "Catalysis vol. VII" (1960), pp. 223, 227.

Primary Examiner—Henry R. Jiles
Assistant Examiner—Dale A. Bjorkman
Attorney, Agent, or Firm—Charles S. Lynch; John E. Miller; Larry W. Evans

[57] ABSTRACT

A process for making 3-cyanopyridine by the vapor phase catalytic reaction of 2-methylglutaronitrile with molecular oxygen.

5 Claims, No Drawings

OXIDATIVE CYCLIZATION OF 2-METHYLGLUTARONITRILE TO 3-CYANOPYRIDINE

This invention relates to a completely new method of preparing 3-cyanopyridine from 2-methylglutaronitrile. Thus, it has been found that 2-methylglutaronitrile can be oxidized and cyclized in one step according to the present invention.

The present method of making 3-cyanopyridine is especially advantageous since the starting material is available in large quantities as a by-product obtained in the making of adiponitrile from acrylonitrile.

3-cyanopyridine is presently an important starting material for the preparation of niacin and niacinamide (vitamin B complex vitamins). The 3-cyanopyridine is prepared from acetaldehyde, formaldehyde and ammonia by known methods.

An object of the present invention is to provide a method for making 3-cyanopyridine from the inexpensive 2-methylgluaronitrile.

Other objects, as well as aspects, features and advantages, of the present invention will become apparent from a study of the present specification including the claims.

According to the present invention there is provided a process which comprises the reaction of molecular oxygen gas with 2-methylglutaronitrile in the vapor phase to produce 3-cyanopyridine.

We regard this reaction per se as our invention since it is a completely new and unreported reaction. We have found that the reaction does not proceed to a detectable degree in the absence of a catalyst. We have found that the solid contact oxidation catalysts which are shown in the specific examples promote the new reaction. There are no doubt other catalysts as yet untried that will be effective, and it is probable that there are solid contact oxidaton catalysts effective in other reactions that are ineffective in the present reaction. However, since we have discovered an unexpected, unreported new reaction we regard the scope of our invention to be the vapor phase catalytic reaction of gaseous oxygen and 2-methylglutaronitrile to yield 3-cyanopyridine, divorced from any designation of a specific catalyst.

The present reaction is conveniently effected by contacting the reactants at temperatures in the range from 300° to 500° C., usually 350° to 475° C., with the solid catalyst for contact times of 0.1 to 20 seconds, usually 0.2 to 8 seconds.

The gaseous molecular oxygen reactant of the invention can of course be diluted with other inert gases such as nitrogen or helium, and air is of course a convenient source of oxygen gas.

The following specific examples of the invention are merely illustrative and are not to be considered in any way limiting.

EXAMPLE 1

2-methylglutaronitrile, (MGN), oxygen and nitrogen were passed through a fixed bed of particulate solid contact catalyst having the empirical formula $Cs_{0.05}K_{0.1}Ni_{2.5}Co_{4.5}Fe_2MnBiCr_{0.5}Mo_{13.2}O_x$ (x is the number of oxygen atoms to satisfy the valences of the other atoms) contained in a 5 cc stainless steel micro reactor tube which was heated in a molten salt bath maintained at 380° C. The mole ratio of the MGN, $O_2$ and $N_2$ was 1.0 MGN/1.3 $O_2$/50 $N_2$ and the contact time was 4 seconds; MGN was introduced with a Sage syringe pump and $O_2$ and $N_2$ flows were regulated by mass flow controllers. Flows through the reactor were allowed to continue for 30 minutes before the collection of any product. Then the reactor effluent was collected into 10 mL of toluene chilled in ice. Internal standard (0.41 mmoles o-xylene) was introduced into the toluene scrubber vessel and mixed thoroughly. Analysis was performed on a Varian 3700 Gas Chromatograph under the following conditions:

column: 10% Carbowax (80/100 Chromosorb W) 6'×⅛"ss
flow rate: 30 mL/min
temperature program:
90° C. for 2 min.
40° C. /min to 190° C.

Standard solutions containing 3-cyanopyridine, 2-methylglutaronitrile and o-xylene (0.41 mmoles) were prepared and used to calculate Response Factors by the following formula:

$$RF = (area\ o\text{-xylene}/area\ X) \times (mmole\ X/mmole\ o\text{-xylene})$$

Typical Response Factors for the components of the standard solutions were as follows:
MGN=1.70
3CP=1.75

The analysis showed that selectivity of conversion of MGN to 3-cyanopyridine was 3.6 percent.

The catalyst was made as follows: A solution of 48.48 g of $Fe(NO_3)_3.9H_2O$, 5.85 g of a 10% aqueous solution of $CsNO_3$, 6.07 g of a 10% (wt.) aqueous solution of $KNO_3$, 43.62 g of $Ni(NO_3)_2.6H_2O$, 78.58 g of $Co(NO_3)_2.6H_2O$, 21,48 g of a 50% (wt.) aqueous solution of $Mn(NO_3)_2$, and 29.11 g of $Bi(NO_3)_3.5H_2O$ in 20 ml of $H_2O$ at 60° C. wasd added to a solution of 139.84 g of $(NH_4)_6Mo_7O_{24}.4H_2O$ and 3.00 g of $CrO_3$ in 400 ml of $H_2O$ at 60° C. with stirring. A yellow slurry formed which was heated at 80° C. with stirring for 1 hour, then at 25° C. for 16 hours. Heating and stirring at 80° C. were continued until the mixture started to thicken, then the slurry was dried at 120° C. The resulting solid was heated at 290° C. for 3 hours and then at 490° C. for 3 hours, then ground and screened to 20–35 mesh and calcined at 500° C. for 3 hours.

EXAMPLE 2

2-methylglutaronitrile, (MGN), oxygen and nitrogen were passed through a fixed bed of particulate solid contact catalyst having the empirical formula 80%$PV_3Mo_{12}O_x$.20%$SiO_2$ (x is the number of oxygen atoms to satisfy the valences of the other atoms) contained in a 5 cc stainless steel micro reactor tube which was heated in a molten salt bath maintained at 370° C. The mole ratio of the MGN, $O_2$ and $N_2$ was 1.0 MGN/1.3 $O_2$/50 $N_2$ and the contact time was 4 seconds; MGN was introduced with a Sage syringe pump and $O_2$ and $N_2$ flows were regulated by mass flow controllers. Flows through the reactor were allowed to continue for 30 minutes before the collection of any product. Then the reactor effluent was collected into 10 mL of toluene chilled in ice. Internal standard (0.41 mmoles o-xylene) was introduced into the toluene scrubber vessel and mixed thoroughly. Analysis effected as in Example 1 showed that 3-cyanopyridine was one of the main liquid products.

The catalyst was made as follows: Into a 1 L beaker containing 400 mL of distilled $H_2O$ was added 11.7 g (0.100 mol) of $NH_4VO_3$ and the resulting mixture heated to 80° C. with stirring. To this mixture was added 3.8 g (0.33 mol) of 85% $H_3PO_4$, and the mixture turned from a cloudy white suspension to a clear red solution. This solution was added at 80° C. with stirring to a mixture of 70.6 g (0.057 mol) of $(NH_4)_6Mo_7O_{24}.4H_2O$ in 250 mL of distilled $H_2O$ also at 80° C. To the resulting clear red solution was added 43.0 g of silica sol (40% $SiO_2$), and the resulting mixture boiled down to ca. 200 mL with vigorous stirring. When the mixture could no longer be stirred, it was heated at 120° C. for 16 hours, 290° C. for 3.0 hours, 425° C. for 16 hours, and finally at 540° C. for 4.0 hours, and the resutling brown solid ground and screened to 20–35 mesh.

EXAMPLE 3

2-methylglutaronitrile, (MGN), oxygen and nitrogen were passed through a fixed bed of particulate solid contact catalyst having the empirical formula $50\%VSb_5FeO_{13}.40\%SiO_2.10\%Al_2O_3$ contained in a 5 cc stainless steel micro reactor tube which was heated in a molten salt bath maintained at 410° C. The mole ratio of the MGN, $O_2$ and $N_2$ was 1.0 MGN/1.3 $O_2$/50 $N_2$ and the contact time was 2 seconds; MGN was introduced with a Sage syringe pump and $O_2$ and $N_2$ flows were regulated by mass flow controllers. Flows through the reactor were allowed to continue for 30 minutes before the collection of any product. Then the reactor effluent was collected into 10 mL of toluene chilled in ice. Internal standard (0.41 mmoles o-xylene) was introduced into the toluene scrubber vessel and mixed thoroughly. Analysis effected as in Example 1 showed that 3-cyanopyridine was one of the main liquid products.

The catalyst was made as follows: A slurry of 47.06 g of alumina powder, 25.0 g of 40% silica sol, and 39.46 g (0.135 mol) of $Sb_2O_3$ in 250 mL of $H_2O$ was heated to 70°–75° C., then a solution of $NH_4VO_3$ (6.33 g, 0.0541 mol) in 180 mL of $H_2O$ heated to 70°–75° C. added and the resulting mixture refluxed for 16 hours. To the boiling solution was then added a solution of 9.42 g (0.0542 mol) of $Fe(OAc)_2$ in 20 mL of $H_2O$, then the volume of the mixture reduced by evaporation and the resulting slurry dried at 110° C. for 16 hours. The resulting solid was heated at 350° C. for 5 hours, ground and screened to 20–35 mesh, and calcined for 3 hours at 530° C.

EXAMPLE 4

2-methylglutaronitrile, (MGN), oxygen and nitrogen were passed through a fixed bed of particulate solid contact catalyst having the empirical formula $80\%VPFeSb_3Mo_{12}O_x.20\%SiO_2$ (x is the number of oxygen atoms to satisfy the valences of the other atoms) contained in a 5 cc stainless steel micro reactor tube which was heated in a molten salt bath maintained at 380° C. The mole ratio of the MGN, $O_2$ and $N_2$ was 1.0 MGN/1.3 $O_2$/50 $N_2$ and the contact time was 0.5 seconds; MGN was introduced with a Sage syringe pump and $O_2$ and $N_2$ flows were regulated by mass flow controllers. Flows through the reactor were allowed to continue for 6 hours before the collection of any product. Then the reactor effluent was collected into 10 mL of toluene chilled in ice. Internal standard (0.41 mmoles o-xylene) was introduced into the toluene scrubber vessel and mixed thoroughly. Analysis effected as in Example 1 showed that 3-cyanopyridine was one of the main liquid products.

The catalyst was prepared as follows: Antimony oxide (14.5 g $Sb_2O_3$) was oxidized in nitric acid (58 cc $HNO_3$) for about 30 minutes with heating and constant stirring. Then added were 3.9 g $NH_4VO_3$, 3.8 g $H_3PO_4$ (85%), 13.5 g $Fe(NO_3)_39H_2O$, 70.6 g $(NH_4)_6.Mo_7O_{24}.4H_2O$ and 68.2 g silica sol (30% $SiO_2$) with heating and stirring being continued until the mixture started to gel. It was then dried at about 130° C. and then heated at 800° F. for 16 hours and 1000° F. for 3 hours. Thereafter, the catalyst was ground and screened to 20–35 mesh.

EXAMPLE 5

2-methylglutaronitrile, (MGN), oxygen and nitrogen were passed through a fixed bed of particulate solid contact catalyst having the empirical formula $Cs_{0.05}K_{0.1}Ni_{2.5}Co_{4.5}Fe_2MnBiCr_{0.5}Mo_{13.2}O_x$ (x is the number of oxygen atoms to satisfy the valences of the other atoms) contained in a 5 cc stainless steel micro reactor tube which was heated in a molten salt bath maintained at 410° C. The mole ratio of the MGN, $O_2$ and $N_2$ and was 1.0 MGN/1.3 $O_2$/50 $N_2$ and the contact time was 2 seconds; MGN was introduced with a Sage syringe pump and $O_2$ and $N_2$ flows were regulated by mass flow controllers. Flows through the reactor were allowed to continue for 30 minutes before the collection of any product. Then the reactor effluent was collected into 10 mL of toluene chilled in ice. Internal standard (0.41 mmoles o-xylene) was introduced into the toluene scrubber vessel and mixed thoroughly. Analysis effected as in Example 1 showed that 3-cyanopyridine was one of the main liquid products. The calalyst preparation was in Example 1.

EXAMPLE 6

2-methylglutaronitrile, (MGN), oxygen and nitrogen were passed through a fixed bed of particulate solid contact catalyst having the empirical formula $80\%PV_3Mo_{12}O_x.20\%SiO_2$ (x is the number of oxygen atoms to satisfy the valences of the other atoms) contained in a 5 cc stainless steel micro reactor tube which was heated in a molten salt bath maintained at 400° C. The mole ratio of the MGN, $O_2$ and $N_2$ was 1.0 MGN/1.3 $O_2$/50 $N_2$ and the contact time was 2 seconds; MGN was introduced with a Sage syringe pump and $O_2$ and $N_2$ flows were regulated by mass flow controllers. Flows through the reactor were allowed to continue for 30 minutes before the collection of any product. Then the reactor effluent was collected into 10 mL of toluene chilled in ice. Internal standard (0.41 mmoles o-xylene) was introduced into the toluene scrubber vessel and mixed thoroughly. Analysis effected as in Example 1 showed that 3-cyanopyridine was one of the main liquid products. The catalyst was prepared as in Example 2.

EXAMPLE 7

2-methylglutaronitrile, (MGN), oxygen and nitrogen were passed through a fixed bed of particulate solid contact catalyst having the empirical formula $Cs_{0.05}K_{0.1}Ni_{2.5}Co_{4.5}Fe_2MnBiCr_{0.5}Mo_{13.2}O_x$ (x is the number of oxygen atoms to satisfy the valences of the other atoms) contained in a 5 cc stainless steel micro reactor tube which was heated in a molten salt bath maintained at 460° C. The mole ratio of the MGN, $O_2$ and $N_2$ was 1.0 MGN/1.3 $O_2$/50 $N_2$ and the contact time was 0.5 seconds; MGN was introduced with a Sage syringe pump and $O_2$ and $N_2$ flows were regulated by mass flow controllers. Flows through the reactor were allowed to continue for 30 minutes before the collection of any product. Then the reactor effluent was collected into 10 mL of toluene chilled in ice. Internal standard (0.41 mmoles o-xylene) was introduced into the toluene scrubber vessel and mixed thoroughly. Analysis effected as in Example 1 showed that 3-cyanopyridine was one of the main liquid products. The catalyst was prepared as in Example 1.

As will be evident to those skilled in the art, modifications of this invention can be made or followed in the light of the foregoing disclosure without departing from the spirit and scop of the disclosure or from the scope of the claims.

We claim:

1. A process for making 3-cyanopyridine by the vapor phase catalytic reaction of 2-methylglutaronitrile with molecular oxygen.

2. A process of claim 1 wherein said reaction is effected at temperatures in the range from 300° to 500° C.

3. A process for making 3-cyanopyridine by reacting 2-methylglutaronitrile with molecular oxygen in the vapor phase in the presence of a solid catalyst at temperatures in the range from 300° to 500° C. and contact times in the range from 0.1 to 20 seconds.

4. A process of claim 3 wherein the temperatures are in the range from 350° to 475° C.

5. A process of claim 4 wherein the contact times are in the range from 0.2 to 8 seconds.

* * * * *